US00PP22870P2

(12) United States Plant Patent
Murakami

(10) Patent No.: US PP22,870 P2
(45) Date of Patent: Jul. 24, 2012

(54) ***SCOPARIA* PLANT NAMED 'SUNTUTULAKI'**

(50) Latin Name: ***Scoparia* sp.**
Varietal Denomination: Suntutulaki

(75) Inventor: Yasuyuki Murakami, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 147 days.

(21) Appl. No.: 12/804,920

(22) Filed: Jul. 30, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para
(74) *Attorney, Agent, or Firm* — C. A. Whealy

(57) ABSTRACT

A new and distinct cultivar of *Scoparia* plant named 'Suntutulaki', characterized by its upright, outwardly spreading and mounding plant habit; vigorous growth habit; freely branching habit; numerous yellow-colored flowers; long flowering period; and good garden performance.

1 Drawing Sheet

Botanical designation: *Scoparia* sp.
Cultivar Denomination: 'SUNTUTULAKI'.

BACKGROUND OF THE INVENTION

The present invention relates to a new and distinct cultivar of *Scoparia* plant, botanically known as *Scoparia* sp. and hereinafter referred to by the name 'Suntutulaki'.

The new *Scoparia* plant is a product of a planned breeding program conducted by the Inventor in Higashiomi, Shiga, Japan. The objective of the breeding program was to create new freely and long flowering *Scoparia* plants with uniquely-colored flowers.

The new *Scoparia* plant originated from a cross-pollination made by the Inventor in July, 2006, in Higashiomi, Shiga, Japan, of a proprietary selection of *Scoparia* sp. identified as code number SC99-1, not patented, as the female, or seed, parent with a proprietary selection of *Scoparia* sp. identified as code number SC86-1, not patented, as the male, or pollen, parent. The new *Scoparia* plant was discovered and selected by the Inventor as a single flowering plant within the progeny of the stated cross-pollination in a controlled environment in Higashiomi, Shiga, Japan in June, 2007.

Asexual reproduction of the new *Scoparia* plant by vegetative cuttings in a controlled environment in Higashiomi, Shiga, Japan since July, 2007, has shown that the unique features of this new *Scoparia* plant are stable and reproduced true to type in successive generations.

SUMMARY OF THE INVENTION

Plants of the new *Scoparia* have not been observed under all possible environmental conditions. The phenotype may vary somewhat with variations in environment such as temperature and light intensity without, however, any variance in genotype.

The following traits have been repeatedly observed and are determined to be the unique characteristics of 'Suntutulaki'. These characteristics in combination distinguish 'Suntutulaki' as a new and distinct cultivar of *Scoparia* plant:

1. Upright, outwardly spreading and mounding plant habit.
2. Vigorous growth habit.

3. Freely branching habit.
4. Numerous yellow-colored flowers.
5. Long flowering period.
6. Good garden performance.

Plants of the new *Scoparia* differ from plants of the female parent selection in the following characteristics:

1. Plants of the new *Scoparia* are more upright than and not as spreading as plants of the female parent selection.
2. Plants of the new *Scoparia* have larger flowers than plants of the female parent selection.

Plants of the new *Scoparia* differ from plants of the male parent selection in the following characteristics:

1. Plants of the new *Scoparia* are not as compact as plants of the male parent selection.
2. Plants of the new *Scoparia* have larger flowers than plants of the male parent selection.

Plants of the new *Scoparia* can be compared to plants of *Scoparia* sp. 'Suntutuki', disclosed in U.S. Plant Pat. No. 16,345. In side-by-side comparisons conducted in Higashiomi, Shiga, Japan, plants of the new *Scoparia* and 'Suntutuki' differed in the following characteristics:

1. Plants of the new *Scoparia* were taller and broader than plants of 'Suntutuki'.
2. Plants of the new *Scoparia* had longer internodes than plants of 'Suntutuki'.
3. Plants of the new *Scoparia* had broader petals than plants of 'Suntutuki'.

BRIEF DESCRIPTION OF THE PHOTOGRAPHS

The accompanying colored photographs illustrate the overall appearance of the new *Scoparia* plant showing the colors as true as it is reasonably possible to obtain in colored reproductions of this type. Colors in the photographs may differ slightly from the color values cited in the detailed botanical description which accurately describe the colors of the new *Scoparia* plant.

The photograph at the top of the sheet comprises a side perspective view of a typical flowering plant of 'Suntutulaki' grown in a container.

The photograph at the bottom of the sheet is a close-up view of a typical flowering plant of 'Suntutulaki'.

DETAILED BOTANICAL DESCRIPTION

The aforementioned photographs and following observations, measurements and values describe plants grown during the early summer in 15-cm containers in an outdoor nursery in Higashiomi, Shiga, Japan and under commercial practice. During the production of the plants, day temperatures averaged 23° C. and night temperatures averaged 13° C. Plants were four months old when the photographs and description were taken. In the following description, color references are made to The Royal Horticultural Society Colour Chart, 2001 Edition, except where general terms of ordinary dictionary significance are used.

Botanical classification: *Scoparia* sp. 'Suntutulaki'.

Parentage:

*Female, or seed, parent*.—Proprietary selection of *Scoparia* sp. identified as code number SC99-1, not patented.

*Male, or pollen, parent*.—Proprietary selection of *Scoparia* sp. identified as code number SC86-1, not patented.

Propagation:

*Type*.—By vegetative cuttings.

*Time to initiate roots*.—About six days at 20° C. to 25° C.

*Time to produce a rooted young plant roots*.—About three weeks at 15° C. to 25° C.

*Root description*.—Fibrous; white in color.

*Rooting habit*.—Freely branching; moderately dense.

Plant description:

*Plant form/habit*.—Upright, outwardly spreading and mounded plant habit; vigorous growth habit; freely branching habit with numerous lateral branches developing per plant.

*Plant height*.—About 16.6 cm.

*Plant width* (*spread*).—About 38.6 cm.

*Lateral branches*.—Length: About 19.2 cm. Diameter: About 1.1 mm. Internode length: About 1.9 cm. Strength: Strong. Texture: Smooth, glabrous. Color: Close to 144A.

Foliage description:

*Arrangement*.—Whorled, simple; sessile.

*Length*.—About 1.9 cm.

*Width*.—About 6.4 mm.

*Shape*.—Roughly lanceolate, pinnately-lobed.

*Apex*.—Acute.

*Base*.—Cuneate.

*Margin*.—Three to five-lobed.

*Texture, upper and lower surfaces*.—Smooth, glabrous.

*Venation pattern*.—Parallel, reticulate.

*Color*.—Developing and fully expanded leaves, upper surface: Close to 137B; venation, close to 138C. Developing and fully expanded leaves, lower surface: Close to 138B; venation, close to 138C.

Flower description:

*Flower type/habit*.—Small single rotate flowers; flowers borne in upper leaf axils; flowers face mostly outwardly; freely flowering habit with about 327 flowers developing per plant.

*Fragrance*.—Similar to anise.

*Natural flowering season*.—Plants begin flowering about four weeks after planting; long flowering period with plants flowering continuously from spring to late autumn in Higashiomi, Shiga, Japan.

*Postproduction longevity*.—Flowers last about seven to ten days on the plant; flowers not persistent.

*Flower buds*.—Height: About 5.1 mm. Diameter: About 2.1 mm. Shape: Ovoid. Color: Close to 144B.

*Flower diameter*.—About 1.1 cm.

*Flower depth*.—About 6 mm.

*Petals*.—Quantity per flower: Typically four in a single whorl; petals fused at the base. Length: About 5.2 mm. Width: About 5.7 mm. Shape: Rounded. Apex: Obtuse. Margin: Entire. Texture, upper and lower surfaces: Smooth, glabrous. Color: Developing and fully expanded petals, upper surface: Close to 7A. Developing and fully expanded petals, lower surface: Close to 7C.

*Sepals*.—Quantity per flower: Typically five in a single whorl, fused at the base; star-shaped calyx. Length: About 3.5 mm to 6 mm. Width: About 1.3 mm to 2 mm. Shape: Lanceolate. Apex: Acute. Base: Obtuse. Margin: Entire. Texture, upper and lower surfaces: Smooth, glabrous. Color, upper and lower surfaces: Close to 144A.

*Peduncles*.—Length: About 1.4 cm. Diameter: About 0.2 mm. Texture: Smooth, glabrous. Color: Close to 144B.

*Reproductive organs*.—Stamens: Quantity per flower: Typically four. Stamen length: About 2.7 mm. Anther shape: Ellipsoidal. Anther size: About 2.5 mm by 0.9 mm. Anther color: Close to 9A. Pollen amount: Moderate. Pollen color: Close to 9C. Pistils: Quantity per flower: One. Pistil length: About 2.8 cm. Stigma shape: Globose. Stigma color: Close to 144A. Style color: Close to 153D. Ovary color: Close to 145C.

*Seed/fruit*.—Seed and fruit development have not been observed.

Disease/pest resistance: Plants of the new *Scoparia* have not been noted to be resistant to pathogens and pests common to *Scoparia* plants.

Garden performance: Plants of the new *Scoparia* have been observed to have good garden performance and tolerate rain, wind and temperatures from about −5° C. to about 35° C.

It is claimed:

1. A new and distinct *Scoparia* plant named 'Suntutulaki' as illustrated and described.

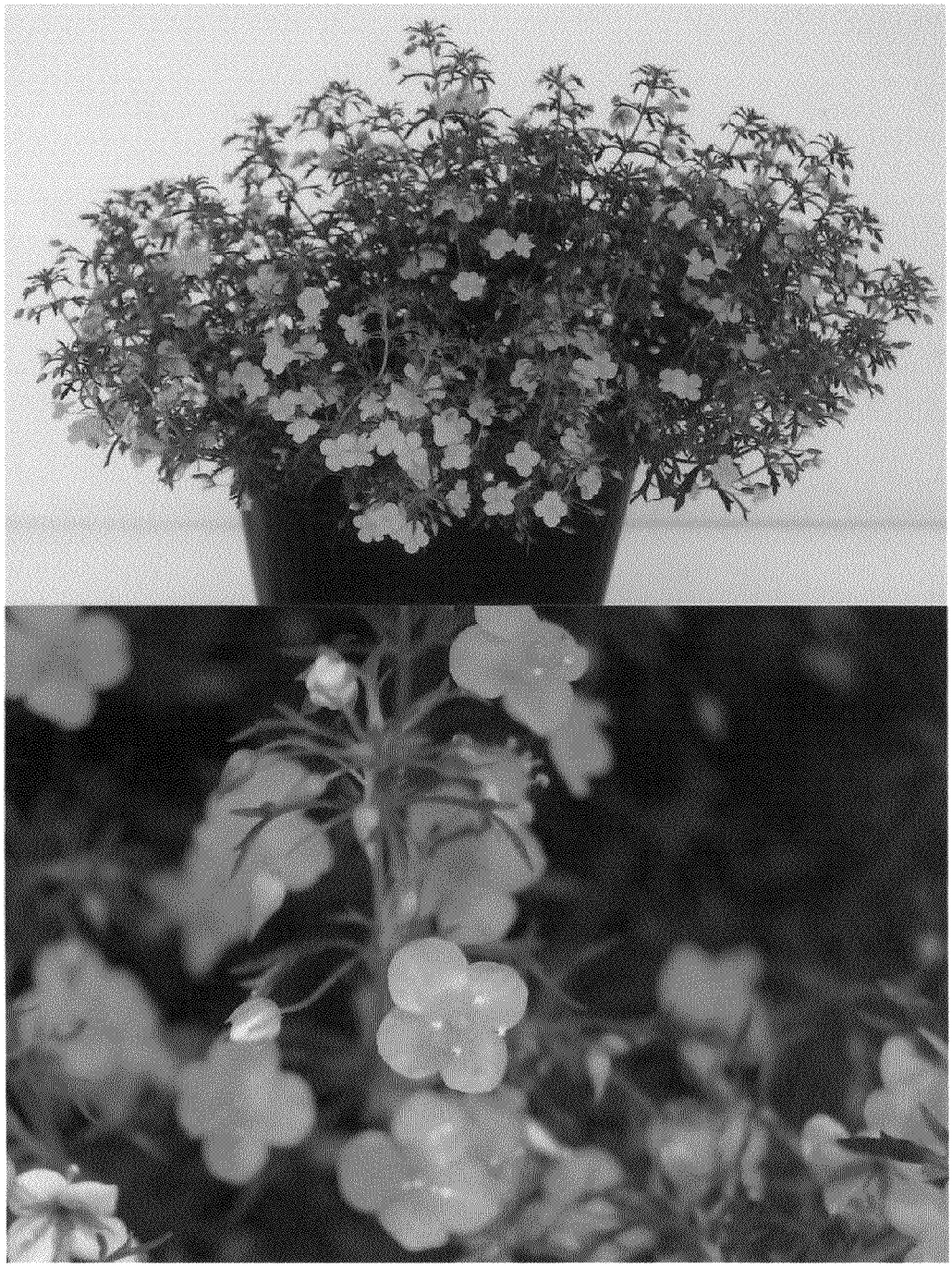

* * * * *